United States Patent
Yu

(10) Patent No.: US 9,896,537 B2
(45) Date of Patent: Feb. 20, 2018

(54) NORBORNANYL ROSIN RESIN AND PROCESS FOR PREPARING SAME

(71) Applicant: Hui Yu, Kansas City, MO (US)

(72) Inventor: Hui Yu, Kansas City, MO (US)

(*) Notice: Subject to any disclaimer, the term of this patent is extended or adjusted under 35 U.S.C. 154(b) by 135 days.

(21) Appl. No.: 13/936,208

(22) Filed: Jul. 8, 2013

(65) Prior Publication Data

US 2015/0011720 A1 Jan. 8, 2015

(51) Int. Cl.
| | |
|---|---|
| C08G 61/12 | (2006.01) |
| C07C 67/04 | (2006.01) |
| C07C 51/353 | (2006.01) |
| C09F 1/04 | (2006.01) |
| C08G 63/553 | (2006.01) |

(52) U.S. Cl.
CPC .......... C08G 61/128 (2013.01); C07C 51/353 (2013.01); C07C 67/04 (2013.01); C08G 61/127 (2013.01); C08G 63/553 (2013.01); C09F 1/04 (2013.01); C07C 2602/42 (2017.05); C07C 2603/68 (2017.05); C08G 2261/3324 (2013.01); C08G 2261/46 (2013.01)

(58) Field of Classification Search
None
See application file for complete search history.

(56) References Cited

U.S. PATENT DOCUMENTS

| | | | | |
|---|---|---|---|---|
| 4,092,283 | A * | 5/1978 | Oishi | C09D 11/10 527/600 |
| 5,194,640 | A * | 3/1993 | Cosgrove | C07C 51/353 530/233 |
| 5,395,866 | A * | 3/1995 | Ross | C08F 290/141 523/512 |
| 6,284,433 | B1 * | 9/2001 | Ichikawa | B41C 1/1016 101/463.1 |
| 6,432,195 | B1 * | 8/2002 | Rathschlag | C09D 5/36 106/417 |
| 2001/0008921 | A1 * | 7/2001 | Matzinger | C08F 257/02 525/290 |
| 2001/0049420 | A1 * | 12/2001 | Matzinger | C08F 265/04 525/329.7 |
| 2003/0144457 | A1 * | 7/2003 | Brinkhuis | C08G 73/0233 528/272 |
| 2012/0052443 | A1 * | 3/2012 | Masuyama | G03F 7/0045 430/281.1 |
| 2013/0317156 | A1 * | 11/2013 | Yu | C07C 69/753 524/356 |
| 2015/0011720 | A1 * | 1/2015 | Yu | C08G 61/127 527/600 |

* cited by examiner

*Primary Examiner* — Peter A Salamon

(57) ABSTRACT

This invention relates to the new norbornanyl rosin resin compositions which are easily obtainable by reacting the norbornenyl compounds or their alpha, beta-unsaturated esters with rosin derivative. In particular, this invention relates to a new process for making hybrid rosin resin suitable for production adhesive, ink, coating, plasticizer, thermoplastic or thermosetting plastic and functional polymers.

3 Claims, No Drawings

NORBORNANYL ROSIN RESIN AND PROCESS FOR PREPARING SAME

BACKGROUND OF THE INVENTION

Field of the Invention

The present invention relates to novel functionalized norbornanyl rosin resin composition, which is produced by reacting substituted norbornenes or their alpha, beta-unsaturated esters with rosin or rosin derivatives. In particular, this invention relates to a novel process for making modified rosin from Diels-Alder adduct, which is easily obtained by reacting diene with dienophile. The invention specifically provides new modified rosin compositions represented by the Scheme-1:

A: The Rosin Modified with Norbornenyl Compound Represented by the General Formula-1

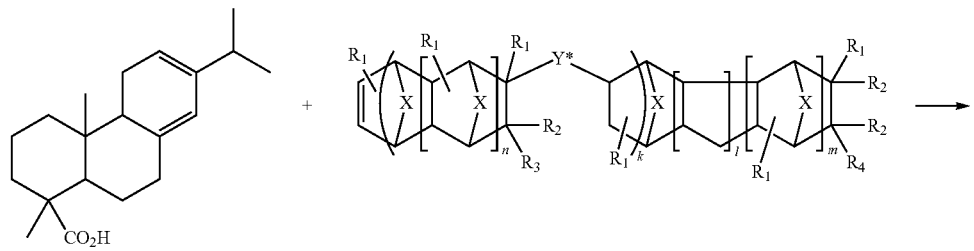

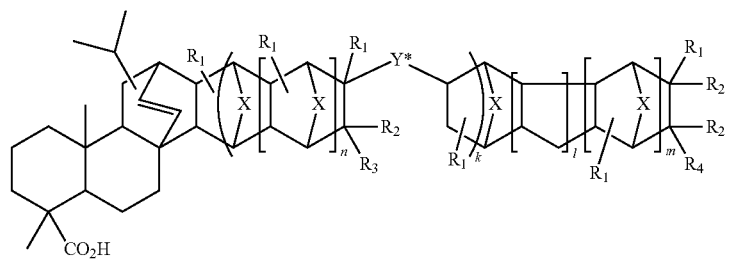

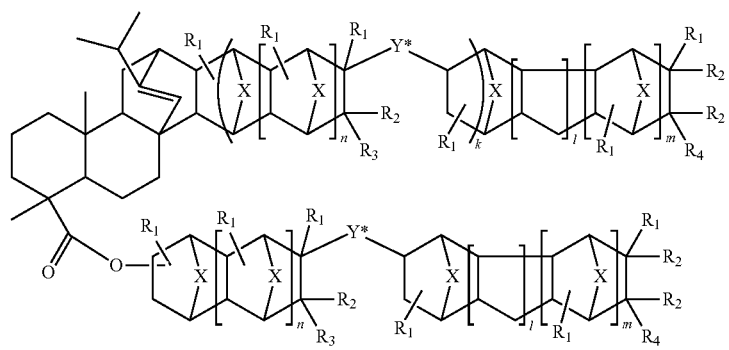

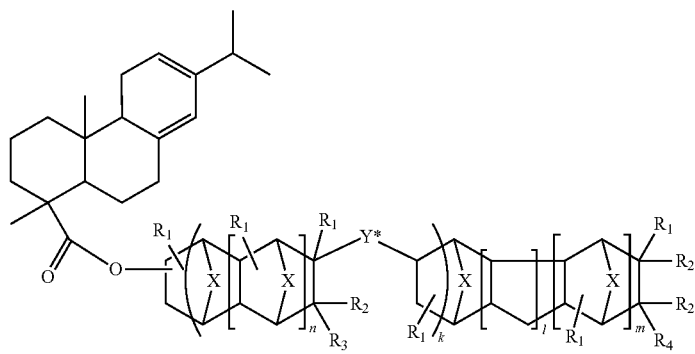

B: The Rosin Modified with Norbornenyl Alpha, Beta-Unsaturated Ester Compound Represented by the General Formula-2

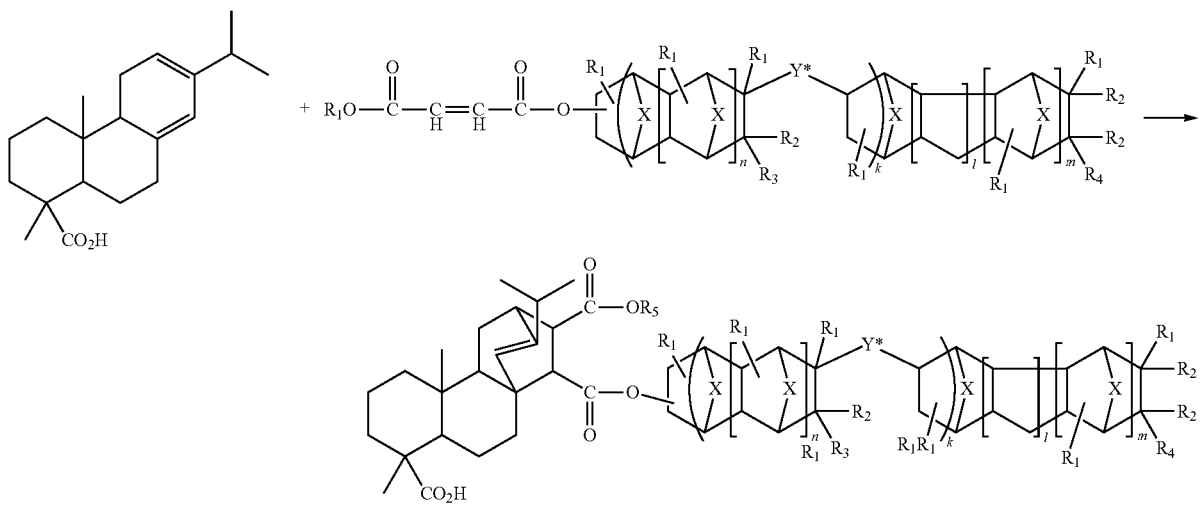

C: The Rosin Modified with Norbornenyl Alpha, Beta-Unsaturated Ester Compound Represented by the General Formula-3

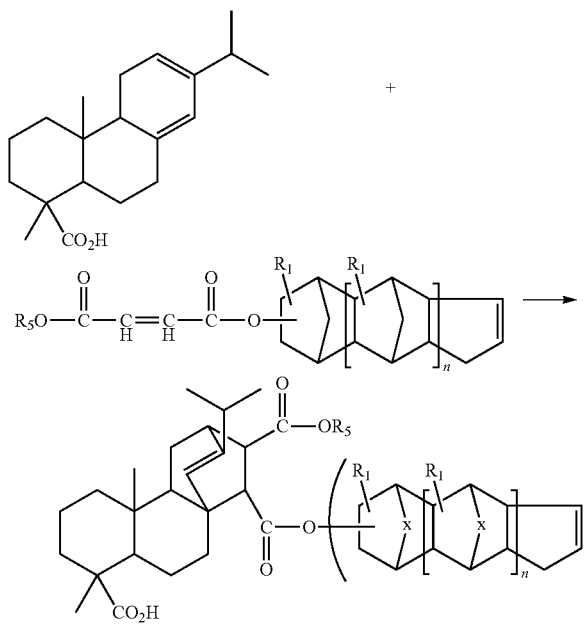

The norbornenyl compounds or their alpha, beta-unsaturated esters represented by the Formula-1, Formula-2 and Formula-3 are prepared from Diels-Alder reaction and/or acid addition reaction.

In the Formula-1, Formula-2, Formula-3, $R_1$ is a hydrogen atom, a methyl, or a hydroxymethyl group; $R_2$, $R_3$, $R_4$ and $R_5$ are the same or different from each other and are independently selected from the group consisting of hydrogen; halogen; hydroxyl; acid (—C(O)OH); ester (—C(O)OR$_a$); formate (—OC(O)H); acid halide (—C(O)Z); aldehyde (—C(O)H); ketone (—C(O)R$_a$); nitro (—NO$_2$); carboxamide (—C(O)NR$_a$R$_b$); amine (—NR$_a$R$_b$); silicone (—SiR$_a$R$_b$R$_c$); cyano (—CN); isocyanate (—NCO); alkoxy (—OR$_a$); phosphonate (—P(O)R$_a$R$_b$); unsubstituted or substituted $C_1$-$C_{100}$ alkyl group, unsubstituted or substituted $C_2$-$C_{100}$ alkenyl group, unsubstituted or substituted $C_2$-$C_{100}$ alkynyl group, unsubstituted or substituted $C_3$-$C_{100}$ cycloalkyl group, unsubstituted or substituted $C_6$-$C_{100}$ aryl group, when it is substituted with one or more substituent group the substituent group selected from a carboxyl, hydroxyl, thiol, halogen, ester, amine, amide, imide, isocyanate, alkyl, alkenyl, alkynyl, haloalkyl, haloalkenyl, haloalkynyl, aryl, haloaryl, aralkyl, haloaralkyl, alkoxy, haloalkoxy, halocarbonyloxy, aryloxy, haloaryloxy, silyl, siloxy, glycidoxy, heterocyclo, carbonate, carboxylate, and quaternary ammonium, $R_2$, $R_3$ and $R_4$ may be acid anhydride groups (—C(O)—O—(O)—) or imide groups (—C(O)—NR$_a$—C(O)—) formed by being bonded to each other when they are the functional groups, X represents oxygen, CH$_2$, or CH$_2$—CH$_2$. k is an integer of 0 to 100; l is an integer 0 to 1; m and n both represent an integer 0 to 5; p is an integer 1 to 1000, Y is a bridge member selected from the group consisting of (—C(O)O—), (—R$_6$—), (—R$_7$C(O)O—), (—C(O)OR$_7$O—), (—C(O)OR$_7$OC(O)—), (—O—), (—OR$_7$O—), (—R$_7$OC(O)OR$_8$—), (—R$_7$C(O)OR$_8$—), and (—R$_7$C(O)R$_8$—), wherein R$_a$, R$_b$ and R$_c$ are independent hydrocarbyl or substituted hydrocarbyl; Z is a halogen atom, R$_6$, R$_7$ and R$_8$ are divalent organic groups selected from substituted or unsubstituted alkanes, alkenes, cycloaliphatic groups, amine and aromatic groups, At least one of the substituents R$_2$, R$_3$, and R$_4$ is a polar functional group containing at least one atom selected from the group consisting of oxygen, nitrogen, phosphorus, sulfur, silicon and boron.

Description of the Related Art

The rosin derivatives and polymers have great economic significance as important intermediates or polymeric materials for the chemical industry. They are particularly attractive because their unsaturated double bonds and carboxylic group afford the functionality for modification to obtain desired properties.

There are some reports regarding preparation of modified rosin derivatives. One method is Diels-Alder reaction of the rosin derivatives. For example, U.S. Pat. Nos. 2,973,332, 3,390,046, 3,562,243, 3,663,523, 5,164,446 and 8,431,303 as well as Chinese patent CN101591238 report the rosin modification with maleic anhydride, fumaric acid and acrylic acid.

Another method is modification of rosin with both cyclic olefin and unsaturated acid. U.S. patent 40922835246998, U.S. Pat. No. 7,262,238; Japanese patent application 1982049067; 2011225750 and European patent EP0816390 claim that modified rosin produced from dicyclopentadiene, unsaturated carboxylic acid and rosin.

There has been no report on the efficient preparation of modified rosin resin containing ridged, bicyclic skeleton derivatives. There is therefore a need for a simple and inexpensive process for preparing rosin based chemical raw materials or polymeric materials containing a bridged ring structure.

SUMMARY OF THE INVENTION

Norbornene derivatives contain bridged ring with extra strain on the bicycloheptene double bond, and are highly reactive for Diels-Alder reaction, hydrocarboxylation, hydroalkoxylation, polymerization and other reactions. The rosin is reacted with unsaturated norbornenyl or their alpha, beta-unsaturated esters to produce modified rosin resin. The produced cyclic rosin resin has bridged, six-member ring with desired properties.

As the raw material the unsaturated norbornenyl compounds or their alpha, beta-unsaturated esters are obtained as Diels-Alder adduct from appropriate dienes and dienophiles. It is also possible to first modify the Diels-Alder adduct to obtain a unsaturated norbornenyl compounds or their alpha, beta-unsaturated esters having desired structure and subsequently react with an appropriate rosin derivative. The modification of Diels-Alder adducts provides a method to optimize the molecular structure of functional bicyclic rosin resin. In this way, the properties of modified rosin resin can easily be varied by changing both the structure and ratio of the Diels-Alder adducts. The norbornene's strained cycloheptene structure is not only reactive for Diels-Alder reaction but also reactive for the carboxylic group of the rosin. This new chemistry will provide great opportunities for industrial synthesis of modified rosin.

The second purpose of this present invention is to provide a process of forming norbornanyl rosin resin. The process may include synthesis a Diels-Alder adduct and subjecting the obtained norbornenyl compound and a multicarboxylic acid to an acid addition or hydroalkoxylation reaction. The acid addition of the norbornenyl compound may be processed in the absence of catalyst. This self-catalytic process eliminates the need to remove the catalyst and can be finished in a one-pot process.

The synthetic strategy of this invention may include three steps:
1. Synthesis of norbornenyl compound by Diels-Alder reaction
2. Synthesis of norbornenyl compound ester by addition of carboxylic acid to norbornenyl ring
3. Synthesis norbornanyl rosin resin by Diels-Alder reaction and addition of carboxylic acid to norbornenyl ring Step 1: Synthesis of Norbornenyl Compound by Diels-Alder Reaction The formation of the substituted norbornene by reacting a dienophile with a diene, such as cyclopentadiene, can be illustrated by the Scheme-2:

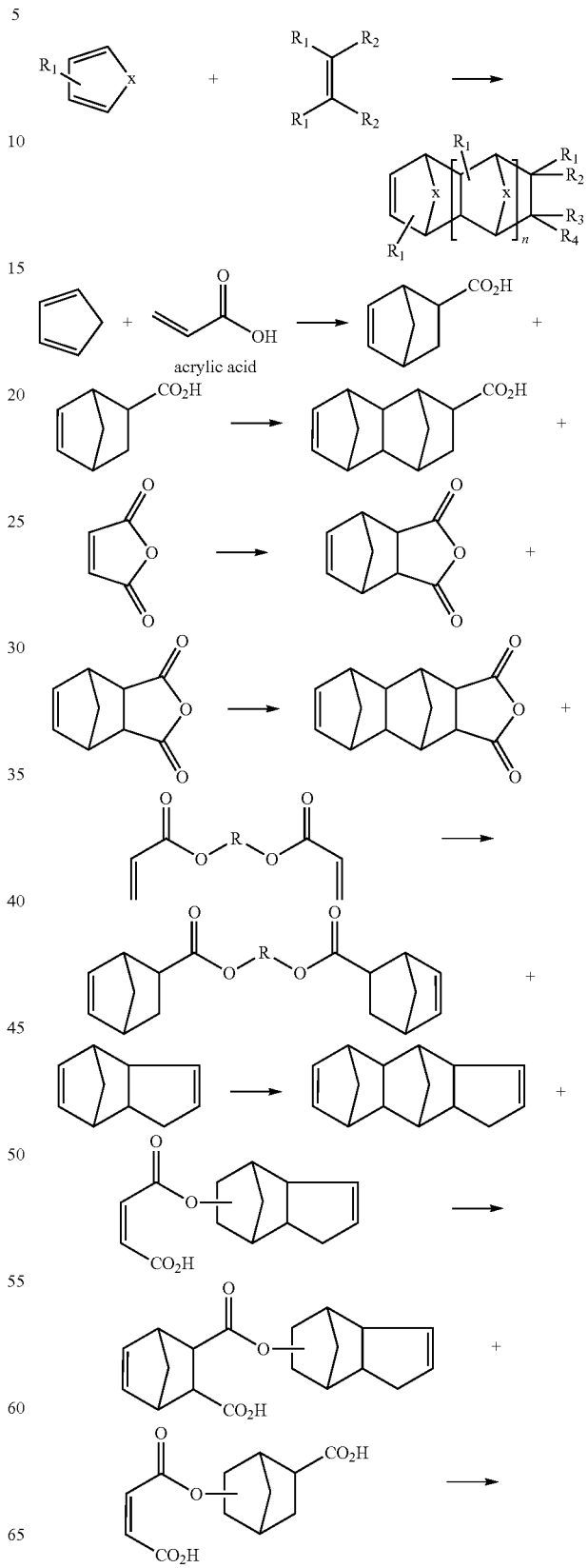

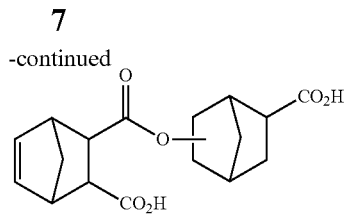

wherein the definitions of $R_{1-5}$, x and n are the same as those in Formula-1.

Step 2: Synthesis of Norbornenyl Compound Ester by Addition of Carboxylic Acid to Norbornenyl Ring The norbornenyl double bond reacts with a mono or multifunctional carboxylic compound to obtain a norbornanyl ester based cyclic compound containing a carboxylic acid or other reactive group. This step can be processed without a catalyst. The resulting product may be directly packaged as chemical raw material or used in the next step for resin synthesis.

The example of addition of carboxylic acid to norbornenyl compound can be illustrated by the Scheme-3:

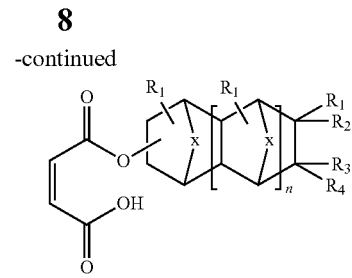

wherein the definitions of $R_{1-5}$, x and n are the same as those in Formula-1.

Step 3: Synthesis Norbornanyl Rosin Resin by Diels-Alder Reaction and Addition of Carboxylic Acid to Norbornenyl Ring Synthesis norbornanyl rosin resin by Diels-Alder reaction and addition of carboxylic acid to norbornenyl ring can be illustrated by the following example Scheme-4:

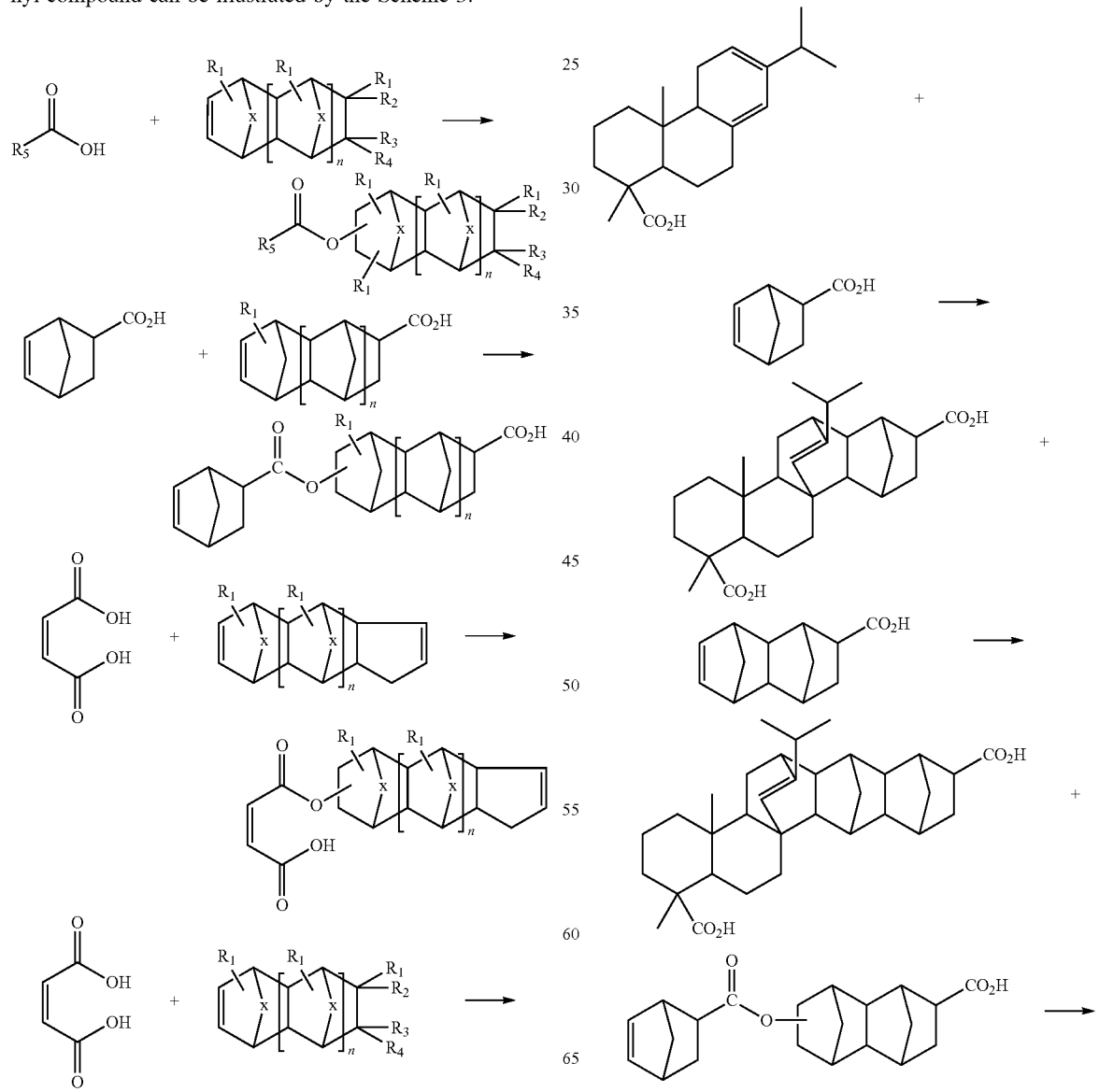

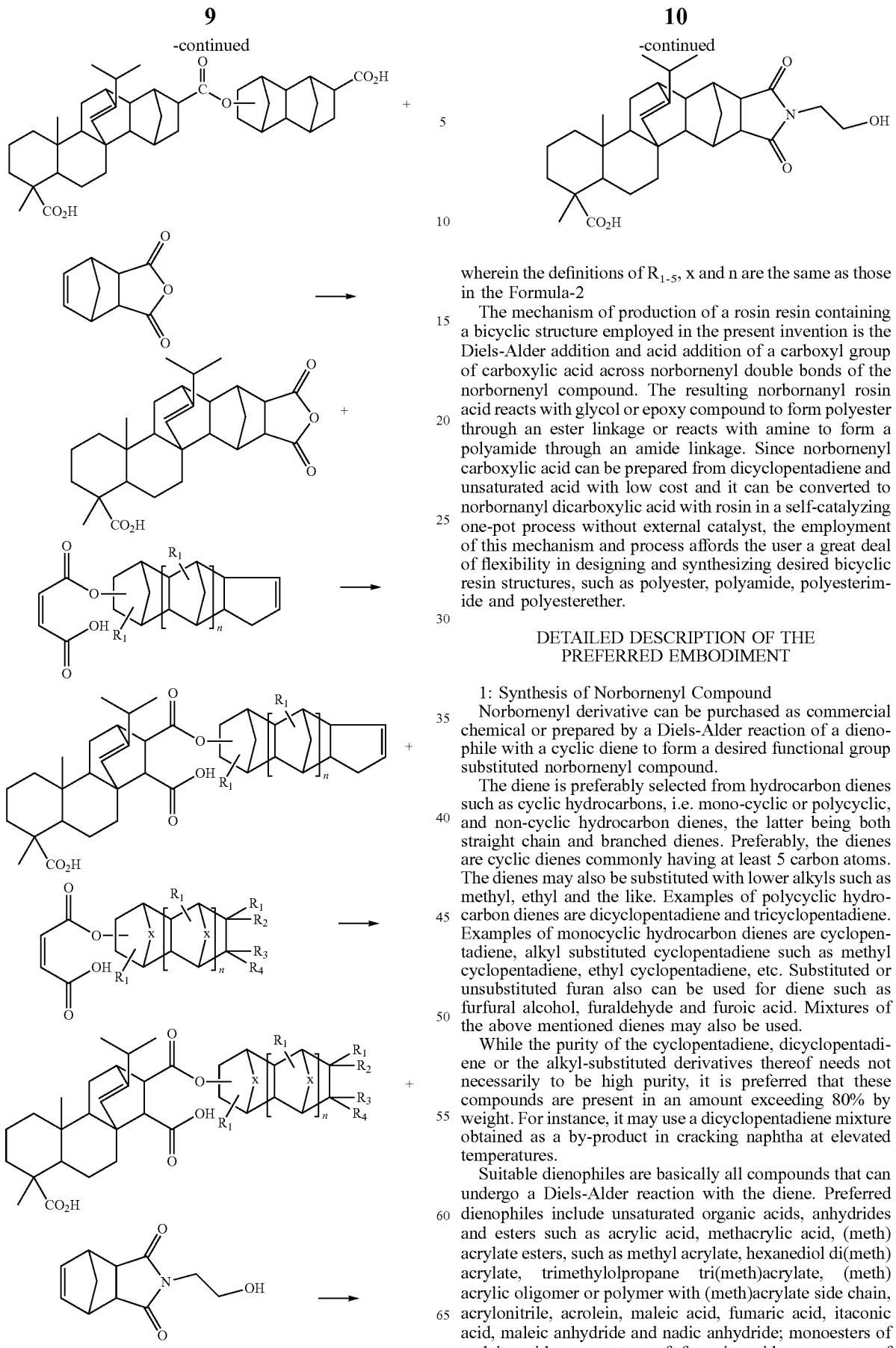

wherein the definitions of $R_{1-5}$, x and n are the same as those in the Formula-2

The mechanism of production of a rosin resin containing a bicyclic structure employed in the present invention is the Diels-Alder addition and acid addition of a carboxyl group of carboxylic acid across norbornenyl double bonds of the norbornenyl compound. The resulting norbornanyl rosin acid reacts with glycol or epoxy compound to form polyester through an ester linkage or reacts with amine to form a polyamide through an amide linkage. Since norbornenyl carboxylic acid can be prepared from dicyclopentadiene and unsaturated acid with low cost and it can be converted to norbornanyl dicarboxylic acid with rosin in a self-catalyzing one-pot process without external catalyst, the employment of this mechanism and process affords the user a great deal of flexibility in designing and synthesizing desired bicyclic resin structures, such as polyester, polyamide, polyesterimide and polyesterether.

DETAILED DESCRIPTION OF THE PREFERRED EMBODIMENT

1: Synthesis of Norbornenyl Compound

Norbornenyl derivative can be purchased as commercial chemical or prepared by a Diels-Alder reaction of a dienophile with a cyclic diene to form a desired functional group substituted norbornenyl compound.

The diene is preferably selected from hydrocarbon dienes such as cyclic hydrocarbons, i.e. mono-cyclic or polycyclic, and non-cyclic hydrocarbon dienes, the latter being both straight chain and branched dienes. Preferably, the dienes are cyclic dienes commonly having at least 5 carbon atoms. The dienes may also be substituted with lower alkyls such as methyl, ethyl and the like. Examples of polycyclic hydrocarbon dienes are dicyclopentadiene and tricyclopentadiene. Examples of monocyclic hydrocarbon dienes are cyclopentadiene, alkyl substituted cyclopentadiene such as methyl cyclopentadiene, ethyl cyclopentadiene, etc. Substituted or unsubstituted furan also can be used for diene such as furfural alcohol, furaldehyde and furoic acid. Mixtures of the above mentioned dienes may also be used.

While the purity of the cyclopentadiene, dicyclopentadiene or the alkyl-substituted derivatives thereof needs not necessarily to be high purity, it is preferred that these compounds are present in an amount exceeding 80% by weight. For instance, it may use a dicyclopentadiene mixture obtained as a by-product in cracking naphtha at elevated temperatures.

Suitable dienophiles are basically all compounds that can undergo a Diels-Alder reaction with the diene. Preferred dienophiles include unsaturated organic acids, anhydrides and esters such as acrylic acid, methacrylic acid, (meth)acrylate esters, such as methyl acrylate, hexanediol di(meth)acrylate, trimethylolpropane tri(meth)acrylate, (meth)acrylic oligomer or polymer with (meth)acrylate side chain, acrylonitrile, acrolein, maleic acid, fumaric acid, itaconic acid, maleic anhydride and nadic anhydride; monoesters of maleic acid, monoesters of fumaric acid, monoester of itaconic acid, monoesters of nadic acid, esters of maleic acid, esters of fumaric acid, esters of nadic acid, ester of itaconic acid, include unsaturated polyester containing esters of maleic acid, esters of fumaric acid, esters of nadic acid, esters of itaconic acid, benzoquinone, vinyl ketones, such as methyl vinyl ketone, nitroalkenes, esters of acetylenedicarboxylic acid, like dimethyl ester of acetylenedicarboxylic acid, dibenzoacetylene, dicyano acetylene, fatty acid and ester of fatty acid.

Other dienophiles include substituted olefin such as norbornene, terpene, styrene, indene, nadic imide and maleimide. Each of the Diels-Alder adducts prepared from the above dienes and dienophiles can be used alone or in combination in the present invention.

The most preferred norbornenyl compound is norbornenyl acid derivative, which is prepared from Diels-Alder reaction of cyclopentadiene and unsaturated carboxylic acid or its anhydride and ester such as acrylic acid, maleic anhydride or maleate, maleic half ester, fumaric acid, fumaric half ester, fumarate. The norbornenyl acid derivative contain both carboxyl group and active double bond and is a very useful A-B type of cyclic monomer for production of norbornanyl oligomer or polymer in this invention.

The conditions that should be used in the Diels-Alder reaction depend upon the cyclic diene and dienophile being used. The Diels-Alder reaction of the above mentioned can be carried out by either a batch system or a continuous system with or without solvent. In a solvent-free batch system, for example, specified amounts of dicyclopentadiene and acrylic acid, maleic anhydride or ester are placed together in a reactor or in a sealed autoclave at a temperature generally ranging from about 150° C. to about 300° C., and more preferably at about 160-250° C. At these temperatures the dicyclopentadiene undergoes a reverse Diels-Alder reaction (crack or de-dimerize) to produce cyclopentadiene which reacts in situ with the dienophile and produces 4+2 adducts. The pressure may vary as needed to keep reactants in the liquid state at the temperature selected and generally will range from about 1 to about 30 atmospheres. Besides being solvent-free, the described procedure allows for almost complete utilization of dicyclopentadiene and avoids production and handling of hazardous cyclopentadiene and residual DCPD polymer.

When cyclopentadiene is used as diene for synthesizing norbornenyl derivatives the reaction temperature is in the range of −20 to 50° C., preferably 10 to 20° C.

Usually the product of a Diels-Alder reaction is a mixture of isomers, including substitution position isomers as well as stereoisomers.

2: Synthesis of Norbornenyl Compound Ester by Addition of Carboxylic Acid to Norbornenyl Ring The norbornenyl derivatives may be reacted with carboxylic acid to form the desired norbornanyl esters for rosin modification. This acidic addition reaction is the hydrocarboxylation of norbornenyl double bond and can be illustrated by the following general Scheme-5:

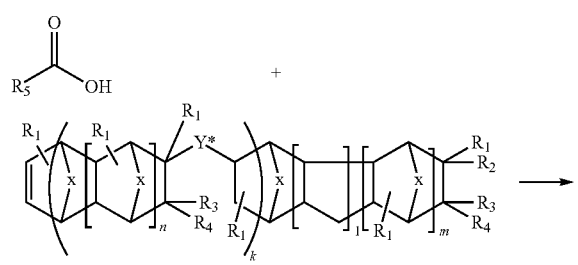

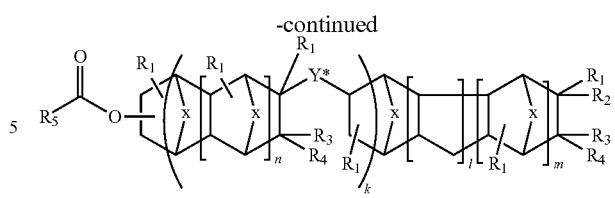

wherein the definitions of $R_{1-5}$, x, y, and k, l, m, n are the same as those in the Formula-1.

In this insertion reaction carboxylic acid across the double bond of norbornenyl ring to form an ester group and it is a self-catalytic acid addition reaction or self-catalytic hydrocarboxylation. There are four types of hydrocarboxylation according to the present invention.

1. Hydrocarboxylation of Norbornenyl Derivative with External Carboxylic Acid

The external carboxylic acid reacts with norbornenyl derivative will lead to an acid adduct, which may be represented by the general Scheme-6:

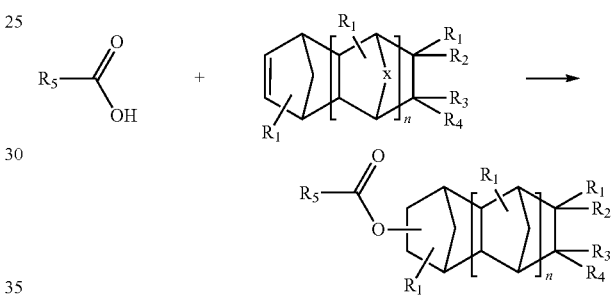

2. Intermolecular Hydrocarboxylation of Norbornenyl Acid Derivative

For carboxyl group functionalized norbornenyl derivative, which is also an A-B type monomer, the intermolecular acidic addition will lead to an oligomer or polymer, which may be represented by general Scheme-7:

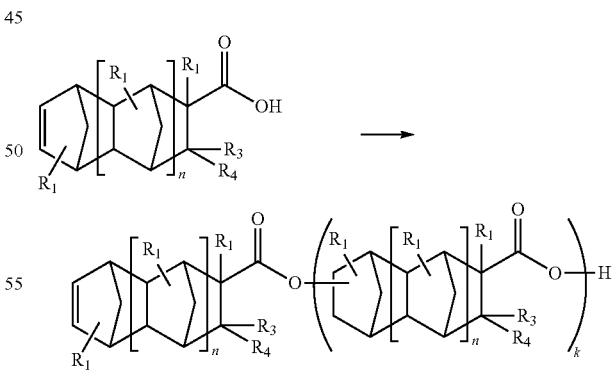

It is a self-addition self-catalytic (SASC) reaction and is a useful method for carbon-carbon bonds construction. In this SASC reaction the carboxyl group acts both as catalyst and nucleophile.

It is possible to prepare norbornenyl oligomer or polymer by SASC process with combination of different acidic norbornenyl derivatives such as Scheme-8:

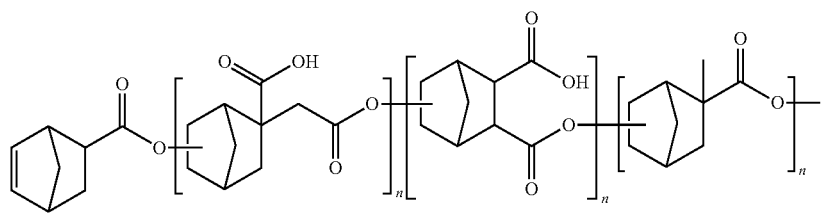

The norbornenyl oligomers prepared by the present invention may be used as not only raw material for rosin modification but also as a cyclic olefin for some other reactions such as hydrocarboxylation, polymerization, hydration and epoxidation.

3 Combined Intermolecular Hydrocarboxylation and External Hydrocarboxylation

When a norbornenyl acid derivative reacts with external carboxylic acid, depending on reaction condition, the product may be an adduct of norbornenyl acid derivative with external carboxylic acid and/or an adduct of norbornenyl acid oligomer with external carboxylic acid. The norbornenyl acid oligomer is the product of intermolecular SASC process of norbornenyl acid derivative as Scheme-9.

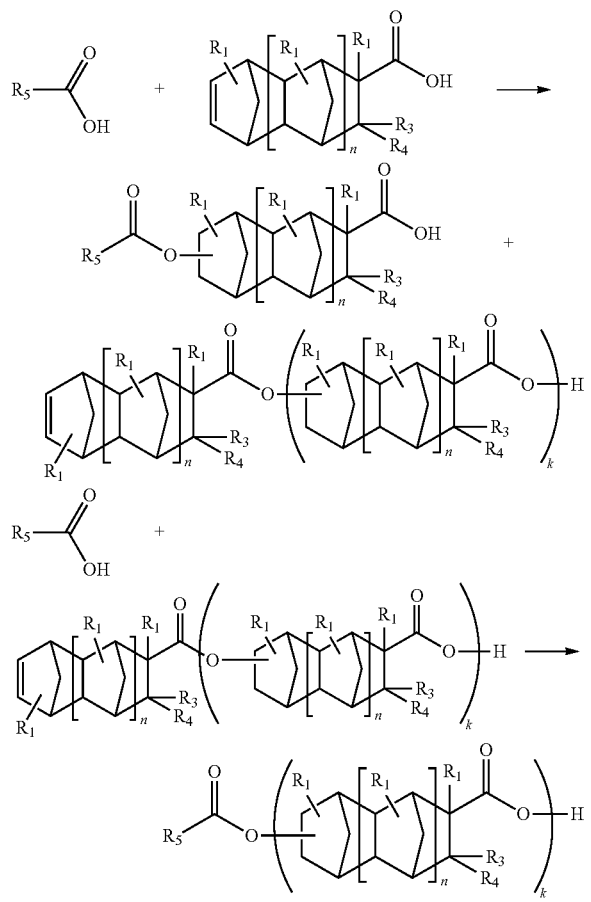

4 Intramolecular Hydrocarboxylation of Norbornenyl Acid Derivative

A norbornenyl acid derivative may undergo a self-addition to produce a norbornanyl lactone such as 2,6-norbornane carbolactone or 2,6-norbornane carbolactone-3-carboxylic acid, which is an intramolecular self-adduct of norbornenyl acid derivative. The yield of intramolecular lactonization is strongly dependent on the reaction condition such as acid activity and temperature.

The other norbornenyl derivative substituted with active hydrogen may also undergo intramolecular cyclization as Scheme-10.

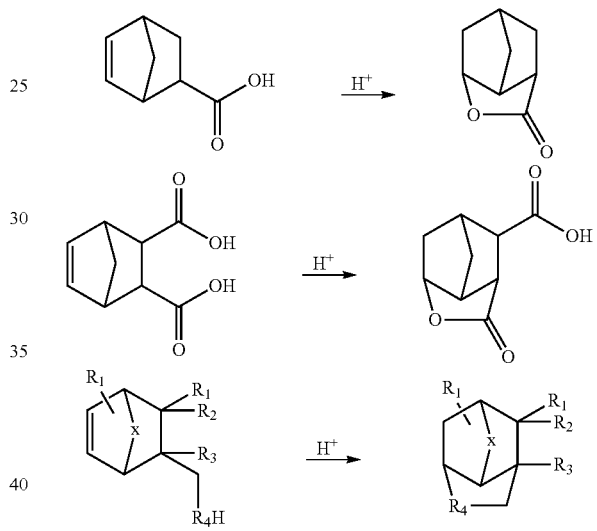

These four types of hydrocarboxylation can be obtained with different reaction formula, procedure and conditions.

The carboxylic acid used for acid addition of the norbornenyl ring composition is suitably a carboxylic acid including saturated or unsaturated mono- or poly-carboxylic acids having up to about 1000 carbon atoms, preferably up to about 100 carbon atoms. Examples of suitable carboxylic acids include 5-norbornene-2-carboxylic acid; nadic acid; maleic acid and fumaric acid. Maleic acid preferably generated in situ by reaction of maleic anhydride with water. For norbornenyl acid derivative, which is an A-B type monomer and enable SASC polymerization, the ratio of external carboxylic acid depends on the amount of reactive norbornenyl ring which is related to degree of SASC polymerization. One advantage of the present invention is the carboxyl functionality and molecular weight of final product can be adjusted by the degree of SASC polymerization of A-B type monomer.

The functional group substituted norbornenyl compounds obtained by the Diels-Alder reaction of cyclopentadienes and dienophile are a mixture of isomers and include the substitution position isomers as well as stereoisomers of each substitution position isomer, which makes a mixture of multi-component isomers. Furthermore the addition of acid to norbornenyl double bond may happen at different positions, and the resulting norbornanyl derivative is a complicated mixture of position isomers and stereoisomers.

These isomers have closely related boiling points and react substantially the same in the formation of the new products of the invention so they can be used as a mixture directly subjected to hydrocarboxylation without further separation.

The process conditions used in the acidic addition reaction depend upon the particular carboxylic acid and norbornenyl derivative used. The acid activity (pKa) of carboxylic acid, and the ring strain, and the substitution position on norbornene ring play an important role in this reaction.

The reaction between the carboxyl acid and norbornene double bond to form the functional group substituted norbornane can be accomplished by heating the components together in a reactor or a sealed autoclave at a temperature generally ranging from about 50° C. to about 300° C., and more preferably at about 110-250° C.

The carboxylic acid with higher acid activity reacts with norbornene double bond at lower temperature and the carboxyl acid with lower acid activity reacts with norbornene double bond at higher temperature. For example the addition reaction temperature between adipic acid (pKa 4.43) and 5-norbornene-2-carboxylic acid is in the range 140-240° C., the reaction temperature between maleic acid (pKa 1.83) and 5-norbornene-2-carboxylic acid or dicyclopentadiene is in the range 90-130° C. In industry maleic anhydride and water are used to produce maleic acid in situ. The anhydride hydrolysis and acid addition reaction substantially occur after the formation of maleic acid. Since both reactions are exothermic it is necessary to control the temperature by proper cooling. At elevated temperature, such as above 130° C. maleic acid will isomerize to fumaric acid (pKa 3.03), which is less reactive acid and a higher temperature, such as 150-200° C. is needed to finish the insertion reaction across a norbornenyl double bond site. Generally the product is the half-ester mixture of maleate and fumarate. The ratio of these two isomers depends on the reaction condition including temperature and catalyst.

The addition reaction of dicyclopentadiene with maleic acid is known. See for example U.S. Pat. No. 6,515,071. Typically the reaction is carried out at a temperature range of 100-130° C., which is high enough to ensure that the dicyclopentadiene reacts with the acid (about 100° C.) but not high enough to cause the dicyclopentadiene to decompose (about 150° C.).

The reaction temperature and time are also related to the molecular weight of reagents, lower temperatures and shorter times are used for the reaction of carboxylic acids or norbornenyl derivative having lower molecular weight. The higher temperatures and longer times are used for the reaction of carboxylic acids or norbornenyl derivative having higher molecular weight.

The Diels-Alder reaction and acid addition reaction of the resulting norbornenyl derivative can be carried out by a multi-step one-pot process. In a one pot-process, for example, specified amounts of dicyclopentadiene and acrylic acid are placed together in a reactor or in a sealed autoclave at a temperature generally ranging from about 150° C. to about 250° C. The pressure may vary as needed to keep reactants in the liquid state at the temperature selected and generally will range from about 1 to about 20 atm. Cyclopentadiene, formed in situ, reacts with the acrylic in a thermodynamically controlled reaction to form Diels-Alder adduct. Maleic acid is charged and heated at about 100° C. to about 200° C. to produce an unsaturated norbornanyl dicarboxylic acid, which may be packaged for raw material or subjected next reaction with rosin for a norbornanyl rosin product.

Solvents such as toluene may be utilized to prevent coagulation of materials or reaction products, but in many cases the cyclic diene or dienophile furnishes sufficient fluidity for the desired addition reaction and the viscosity of the product is low in the reaction temperature. For a manufacturing solvent-free one-pot process, it is preferred to use diene, dienophile or carboxylic acid to work as both reagent and solvent.

The reaction should occur under inert condition by purging with nitrogen. The reaction may be accelerated by using acidic catalysts, for instance sulfuric acid, phosphoric acid, triflic acid, borium trifluoride or complex compounds thereof; the use of a catalyst, however, is not absolutely necessary. A thermal-polymerization preventing agent, such as hydroquinone and 4-methoxyphenol, can be added to the reaction system.

It is convenient to check the progress of converting norbornenyl derivative to norbornanyl ester by testing the acid number in the present invention. The drop in acid number of the products indicates the consumption of the carboxylic acid. This results from the addition of carboxyl group across double bonds on norbornene ring to produce norbornanyl esters.

The norbornanyl ester derivative composition according to the present invention suitably has an acid number 1-500, more preferably about 10-250, and with molecular weight from 100-50000, more preferably about 150-2000.

After the completion of the reaction, the obtained norbornanyl ester derivative can be utilized directly as the raw material as is, or the reaction product can be recovered by removing volatile materials such as the unreacted materials, low boiling substances, and the solvent when employed. It may also be purified by any suitable means, if necessary. For example, after the reaction is completed, water and an organic solvent such as toluene can be added to the resulting reaction mixture, the reaction product is extracted into the oil layer and isolated from the reaction mixture, after which the oil layer containing the reaction product is washed, isolated and concentrated under reduced pressure to obtain a purified product. Furthermore, if necessary, the resulting product can be subjected to vacuum distillation or crystallization purification to obtain a further purified product. The physical state of the product can be solid or liquid at ambient temperature depending largely on the types of reactants used.

For a one-pot process the resulting norbornenyl compound ester will be directly subjected to the next reaction with rosin.

The carboxyl acid substituted norbornenyl derivative molecule possesses two chemically reactive centers, the double bonds and the carboxyl group. Many modifications in structure and numerous derivatives are obtainable from the two functional groups. For example acid addition of maleic acid with 5-norbornene-2-carboxylic acid will lead to an unsaturated dicarboxylic acid with a molecular weight 254 and an acid number of 442 mg KOH/g. If 5-norbornene-2-carboxylic acid is heated for SASC oligomerization before reaction with maleic acid, the acid addition of maleic acid with this norbornenyl oligomer will lead to an unsaturated dicarboxylic acid with a higher molecular weight and a lower acid number. In this way it is possible to design and synthesize cyclic dicarboxylic acid with different acid number for rosin modification. The acid addition of modified and unmodified Diels-Alder adduct can be illustrated by the following Scheme-11:

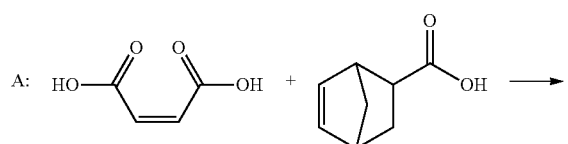
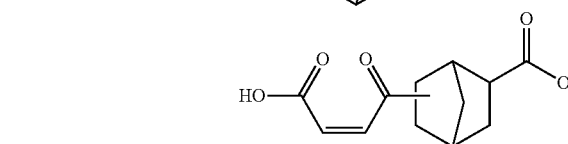
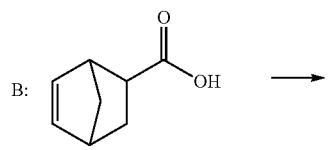

In the present invention the maleic acid monoester (maleic acid half ester) is a versatile dienophile, which is easily prepared from reaction of maleic anhydride with monohydric or multihydric compound or from the addition of maleic acid with unsaturated double bond. One method used in this invention is that maleic acid is used to insert the double bond of Diels-Alder adduct to produce norbornanyl maleic acid half ester; the resulting half ester is subjected Diels-Alder reaction with a diene to produce a new Diels-Alder adduct, which may be subjected to acidic addition again with another maleic acid to produce new maleic acid half ester. This process is called "Double Addition Recycle" (DAR) process, which means Diels-Alder addition and unsaturated acid addition is repeatedly used until a desired norbornanyl polyacid is obtained. DAR process can be represented by the Scheme-12.

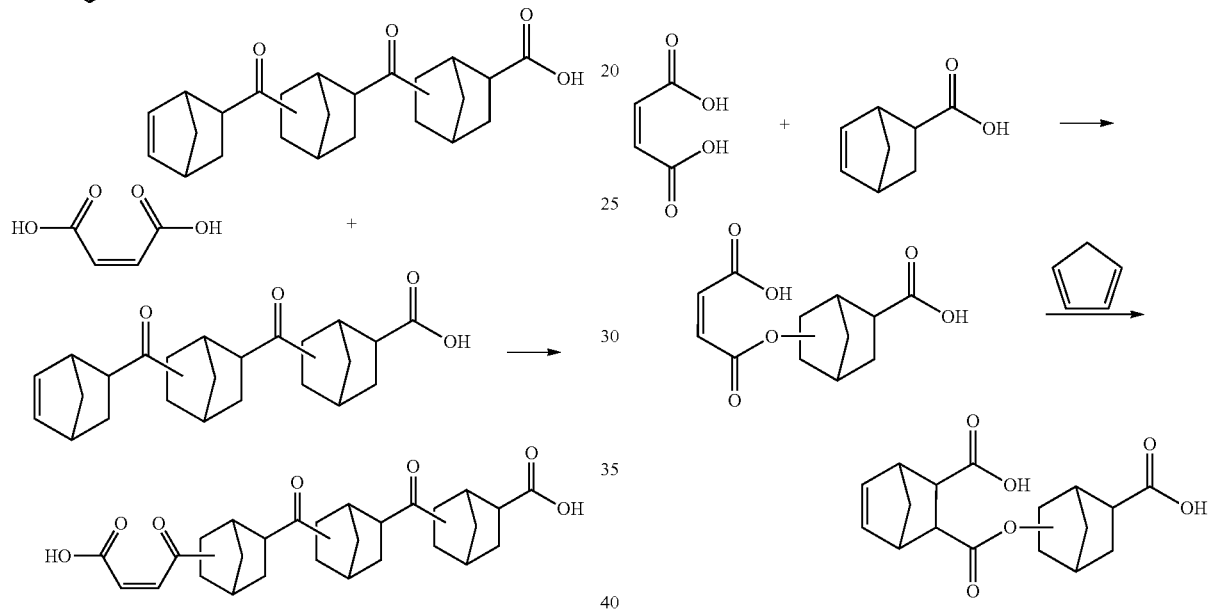

Scheme-13:

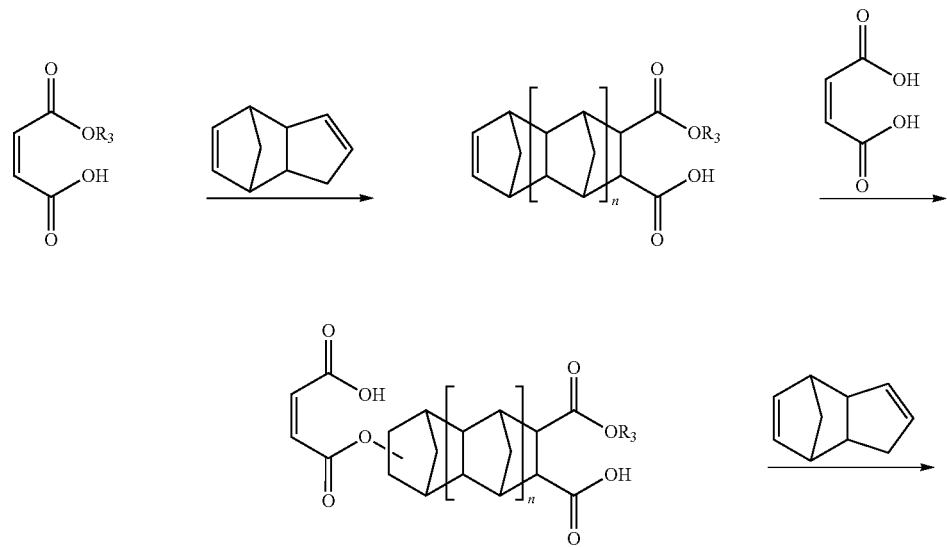

-continued

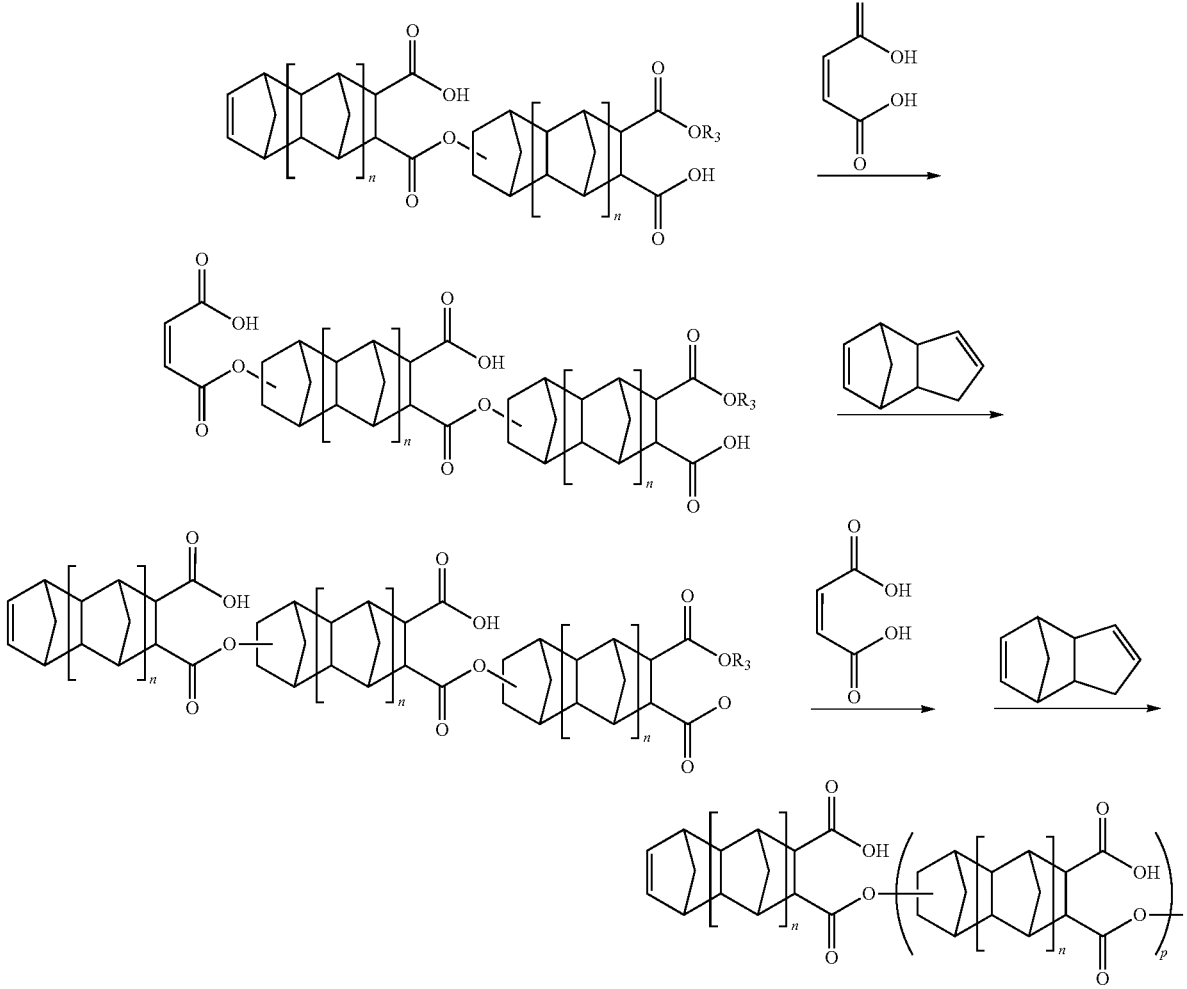

It is also possible to prepare a norbornanyl polyester from dicyclopentadiene and maleic acid in a one-pot process. For example one mole of maleic acid is heated with two moles of dicyclopentadiene to form a norbornenyl dicarboxylic acid half ester, which undergoes an intermolecular acid addition to form a norbornenyl oligomer. It is an economic method to produce DCPD-Maleic acid based oligomer for rosin modification as represented by the following Scheme-14.

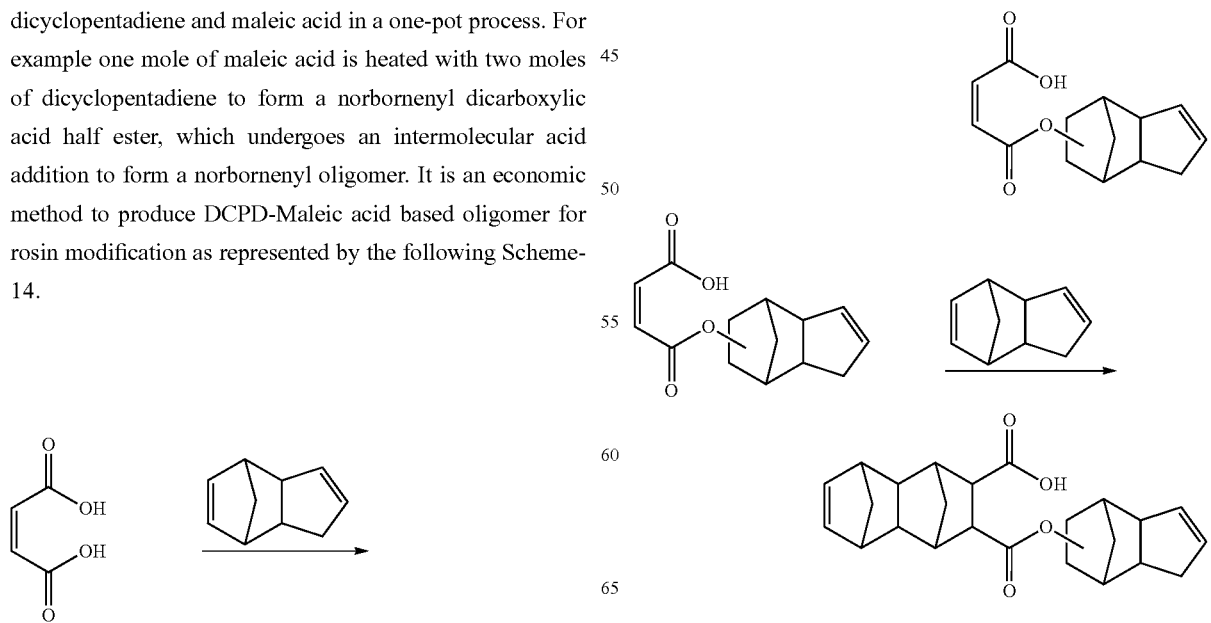

Diels-Alder adduct or norbornenyl derivative itself, which is prepared from diene and dienophile, can be used as dienophile. As a dienophile, the reactivity of the norbornenyl derivative is determined by its substituted group on the ring and molecular weight.

The carboxylic group exerts a great influence upon Diels-Alder reaction and the reactivity of the norbornenyl ring double bond. The carboxylic group of maleic half ester favors cyclopentadiene addition to form a norbornenyl acid derivative.

3: Synthesis Norbornanyl Rosin Resin by Diels-Alder Reaction and Addition of Carboxylic Acid to Norbornenyl Ring The third step reactions are Diels-Alder reaction and acid addition, the norbornenyl compound or its alpha, beta-unsaturated ester obtained in the second step reaction is reacted with rosin to form the desired modified rosin resin. The cyclic double bonds of norbornenyl derivative are reactive for both the diene group and carboxylic group of the rosin. This reaction can be illustrated by the following example Scheme-15:

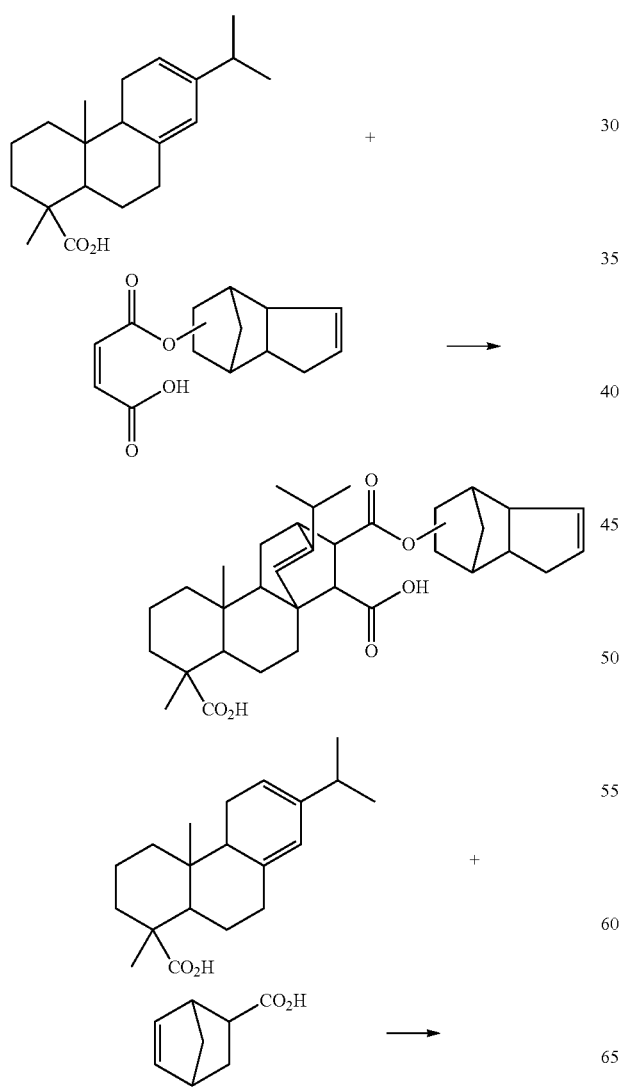

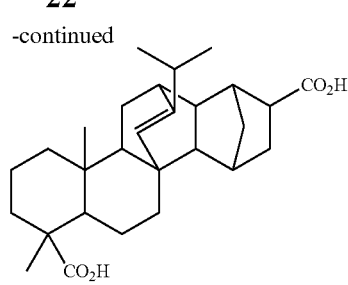

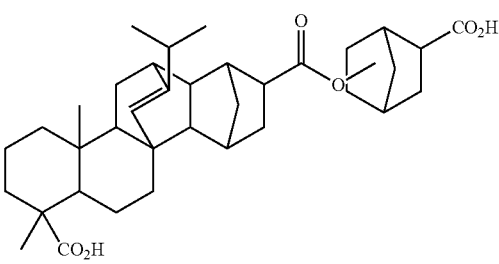

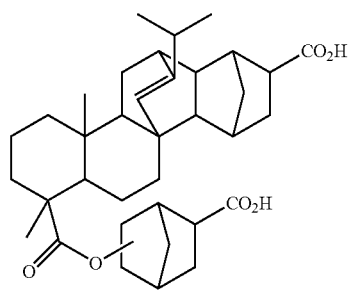

The norbornanyl rosin resin may be prepared using conventional procedures and reaction conditions known to the art. In general, the rosin is first heated to 150-260° C. to melt and remove water or volatile compound. Thereafter the commercial or prepared norbornenyl compound or its unsaturated ester is added and the mixture is reacted for 2-20 hours. For an industry one-pot process the mixture of diene and dienophile may be added to the melted rosin in 100-300° C. in 1-8 hours and the resulting mixture is maintained at this temperature for around 2-6 hours to obtain the desired with an desired acid value and soft point. The reaction is preferably conducted under a nitrogen atmosphere and during the final stages of the reaction a vacuum is applied to the system to facilitate removal of the unreacted compound and any other volatile materials.

In preparing the modified rosin in accordance with the process of this invention, the molecular weight, viscosity, acid or hydroxyl number, glass transition temperature and softening point of the resulting modified can be adjusted by a suitable choice of the combination of the diene/dienophile, structure, ratio, reaction temperature and reaction time.

When multicarboxylic acid substituted norbornanyl rosin resin is subsequently esterified with one or more hydroxyl and/or epoxy compounds a rosin ester oligomer or polyester is formed. Depending on the application the polyester may have different molecular weight and chain end group.

According this invention the norbornanyl rosin is reacted with hydroxyl and/or epoxy compounds with or without extra maleic acid, fumaric acid, and other dicarboxylic acid to form a saturated or unsaturated polyester or polyesterimide containing norbornanyl rosin ring as shown in the following example Scheme-16:

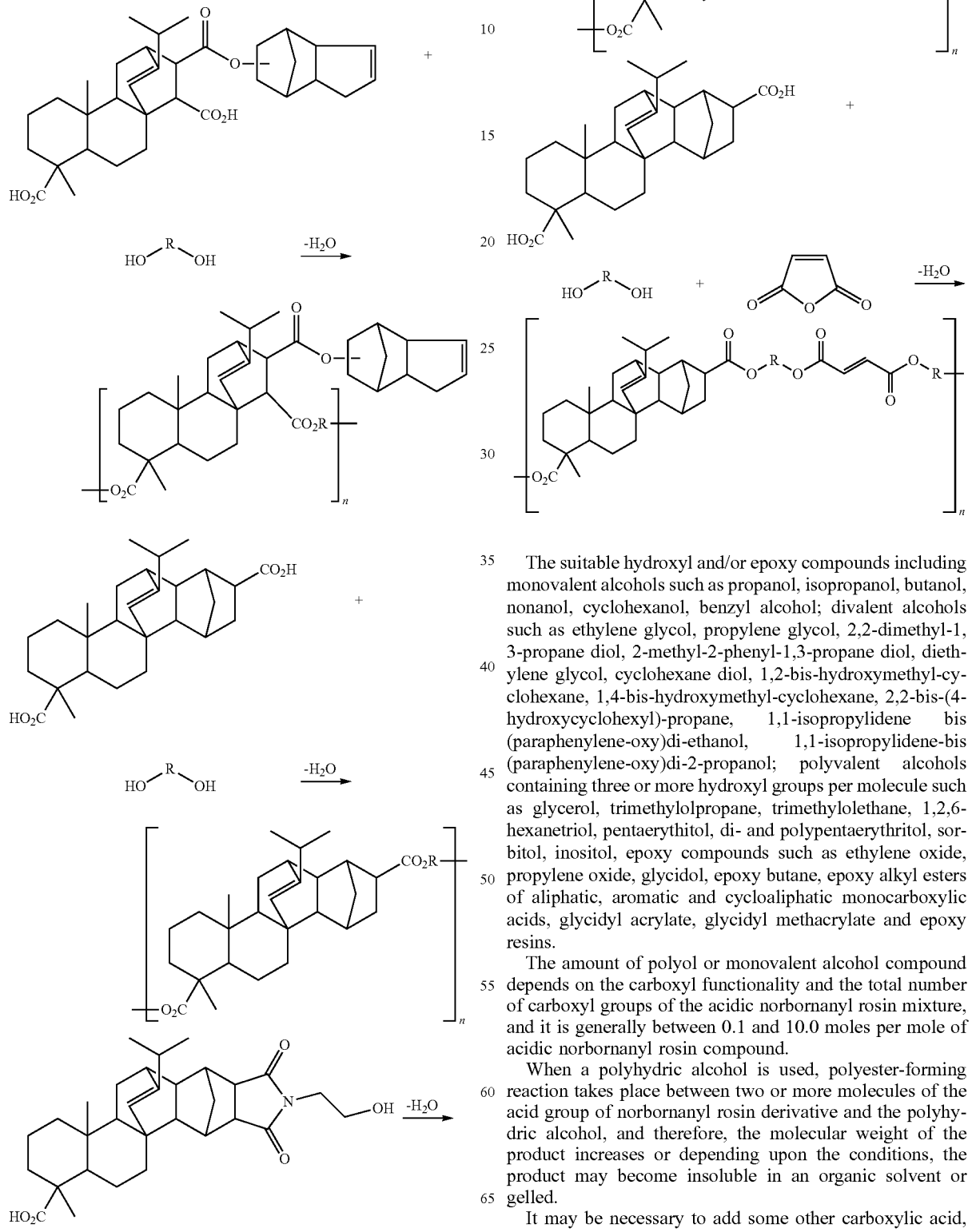

The suitable hydroxyl and/or epoxy compounds including monovalent alcohols such as propanol, isopropanol, butanol, nonanol, cyclohexanol, benzyl alcohol; divalent alcohols such as ethylene glycol, propylene glycol, 2,2-dimethyl-1,3-propane diol, 2-methyl-2-phenyl-1,3-propane diol, diethylene glycol, cyclohexane diol, 1,2-bis-hydroxymethyl-cyclohexane, 1,4-bis-hydroxymethyl-cyclohexane, 2,2-bis-(4-hydroxycyclohexyl)-propane, 1,1-isopropylidene bis (paraphenylene-oxy)di-ethanol, 1,1-isopropylidene-bis (paraphenylene-oxy)di-2-propanol; polyvalent alcohols containing three or more hydroxyl groups per molecule such as glycerol, trimethylolpropane, trimethylolethane, 1,2,6-hexanetriol, pentaerythitol, di- and polypentaerythritol, sorbitol, inositol, epoxy compounds such as ethylene oxide, propylene oxide, glycidol, epoxy butane, epoxy alkyl esters of aliphatic, aromatic and cycloaliphatic monocarboxylic acids, glycidyl acrylate, glycidyl methacrylate and epoxy resins.

The amount of polyol or monovalent alcohol compound depends on the carboxyl functionality and the total number of carboxyl groups of the acidic norbornanyl rosin mixture, and it is generally between 0.1 and 10.0 moles per mole of acidic norbornanyl rosin compound.

When a polyhydric alcohol is used, polyester-forming reaction takes place between two or more molecules of the acid group of norbornanyl rosin derivative and the polyhydric alcohol, and therefore, the molecular weight of the product increases or depending upon the conditions, the product may become insoluble in an organic solvent or gelled.

It may be necessary to add some other carboxylic acid, acid anhydride or diester to adjust the structure. Examples of acid, anhydrides and diester suitable in the above reaction are dimethyl terephthalate, isophthalic acid, phthalic anhydride, succinic anhydride, maleic anhydride, hexahydrophthalic anhydride, tetrahydrophthalic anhydride, trimellitic anhydride, adipic acid, benzoic acid, fatty acid, 2-ethylhexanoic acid, and rosin acid.

The polyester composition comprises at least 5% by weight of the norbornanyl rosin derivative, preferably at least 10 weight %, most preferably at least 25 weight %.

The polyester of the present invention is readily prepared by thermally reacting the above ingredients simultaneously or in consecutive stages at a temperature of 50-300° C., preferably 80-250° C. The reaction may be carried out in the presence of an organic solvent and catalyst or in the absence of the solvent and catalyst. The water formed in the esterification reaction may be removed in the known way, and is generally done by purge with nitrogen or azeotropic distillation with the use of organic solvents such as toluene or xylene.

The progress of polycondensation may be checked by acid number test, depending on the final application the acid number of the cyclic polyester may be in the range 0-200 mg KOH/g. For adhesive application the acid number suitably from 0 up to about 150 mg KOH/g, for the alkyd or thermoset plastic applications the acid number suitably from about 5 up to about 50 mg KOH/g. To be used as polyester polyol for polyurethane formulation the polyester should contain no or very little carboxylic acid group and with an acid number 10 mg KOH/g or less.

The polyester obtained by the above method may have a softening point of 10-200° C. When the polyester is desired to be used for preparing printing ink the softening point should be 100-130° C. If the softening point is lower than 100° C., the resulting printing ink causes frequent misting and suffers from an extreme reduction in drying speed, and blocking tends to occur.

The weight average molecular weight of the resulting polyester is in the range of from about 300 up to about 500000. For fiber and plastic applications suitably from about 30000 up to about 300000 and for coating and thermoset plastic applications suitably from about 500 up to about 50000.

The present invention relates to a novel polyesterimide, which is prepared by polycondensation of nadic imide based norbornanyl rosin carboxylic acid and polyol or a hydroxyalkyl nadimide based norbornanyl rosin carboxylic acid self polycondensation.

Nadic imide or hydroxyalkyl nadimide is prepared from the reaction of nadic anhydride, methyl nadic anhydride with amine. The examples of useful amines include ethanolamine, methylamine, aniline, ethylenediamine, 1,2-propylenediamine, 1,3-propylenediamine, tetramethylenediamine, pentamethylenediamine, hexamethylenediamine, octamethylenediamine, 2-methyl-1,5-pentanediamine, and mixtures thereof.

The rosin polyester or polyesterimide prepared by above methods of this invention may be used as solid such as powder for binder or may be dissolved in solvent or monomer. For coating application the polyester may be dissolved in solvent such as petroleum distillate, ester, glycol ether, alcohol, ketone and white spirit as solvent-borne coating. Examples include benzene, toluene, xylene, ethanol, isopropanol, acetone, ethyl methyl ketone, isobutyl methyl ketone, cyclohexanone, ethyl acetate, butyl acetate. Water may be used as diluent for water-borne cyclic polyester paints.

The reactive rosin polyester prepared in this invention may be diluted with reactive solvent or monomer to form a curable composition under the action of heat, initiator or UV radiation.

The reactive solvent or monomer used in the present invention is preferably an unsaturated compound having one or more polymerizable double bonds in one molecule. Examples of reactive solvent include styrene, (meth)acrylic acid and esters thereof, such as methyl (meth)acrylate, ethyl (meth)acrylate, 2-hydroxyethyl (meth)acrylate, (meth)acrylic acid, ethylene glycol di(meth)acrylate, trimethylolpropane tri(meth)acrylate, oligoester (meth)acrylate, urethane (meth)acrylate oligomer, (meth)acrylic-modified epoxy oligomer, epoxy-modified acrylic urethane oligomer, (meth)acrylate oligomer, dialkyl fumarate, monoalkyl fumarate, dialkyl maleate, monoalkyl maleate. These compounds may be used alone or in combination.

The amount of the reactive solvent or monomer used in the present invention is usually 60% by weight or less. The resulting polyester may be blended with other resin or formulated with different pigment and filler, such as titanium dioxide, talcs, clays or different additives, such as catalyst, stabilizer, and thickener. When reinforced with carbon fiber or fiberglass the curable polyester may be used to manufacture reinforced thermoset plastic.

According to present invention the production above-described functional norbornanyl rosin resin may be adapted by carrying out the two or three reaction steps in a one-pot process, which is desirable to address economic and environmental concerns.

The synthesis of norbornenyl compound or its alpha, beta-unsaturated ester as raw material and synthesis of modified rosin resin may be done in two or three steps with separated reactors. The process is also preferably carried out as a one-pot process, i.e. the Diels-Alder reaction and acid addition for prepare norbornenyl compound or its ester and Diels-Alder reaction for prepare norbornanyl rosin resin are carried out in one and the same reaction vessel without isolation of the intermediates. If final product is a rosin based polyester it is prefer to carry out Diels-Alder reaction, acid addition of Diels-alder adduct and polycondensation of acidic norbornanyl rosin all of three reactions in the same reactor without isolation of the intermediates.

In this one-pot process maleic acid can be prepared in situ, or one-pot, from hydrolysis of maleic anhydride. Cyclopentadiene can be prepared in situ from cracking of dicyclopentadiene. Some reactants may work as both reactant and solvent or reactant and catalyst. For example dicyclopentadiene may works as solvent and diene for Diels-Alder reaction, maleic acid may works as dienophile for Diels-Alder reaction and as carboxylic acid for addition the resulting norbornene derivative, rosin may first works as solvent and heat transfer medium for cracking of dicyclopentadiene and follows by reacting with carboxyl diene compound to form a modified oligomer.

In this one-pot process the different reactions may simultaneously happen. For example when the solution of acrylic acid/dicyclopentadiene is feed into rosin at 220° C. in addition to the Deals-Alder reactions of dienophile double bond with the cyclopentadiene from decomposition of dicyclopentadiene, carboxyl acid groups from both 5-norbornene-2-carboxylic acid and rosin acid also undergo typical acid insert double bond reaction of resulting norbornene rings, i.e. acid addition. As the result of Diels-Alder and hydrocarboxylation the molecular weight of the product increased and acid number of product decreased. In current industry rosin is modified with acrylic acid, maleic anhydride or fumaric acid and the basic reaction is Diels-Alder reaction, and the modification ratio is depends on the ratio of levopimaric acid in the rosin. In the present invention rosin is modified by not only Diels-Alder reaction but also hydrocarboxylation. It is a feature of the present invention to provide economical one-pot process for preparation of modified rosin resin with adjustable properties by this a new chemistry.

Industry Application

The functional norbornanyl rosin resin provided by this invention has great economic significance as important versatile intermediates for the chemical industry.

With appropriate choices for the diene, dienophile, ratio and reaction condition the norbornanyl rosin resin prepared by this new process can be useful raw materials in production of polyester, polyesterimide, polyamide for plastic, fiber coating, ink, adhesive, sizing agent etc.

The new norbornanyl rosin dicarboxylic acids can be used to prepare functional polymer such as reactive polyester. The reactive polyester can be prepared by esterification reaction or the ester-exchange reaction of a rosin acid derivative thereof with an alcohol component of a polyhydric alcohol. Depending on the ratio of acid to hydroxyl, the obtained polyester will have a hydroxyl group and/or a carboxyl group at the terminals, and these terminal groups are reactive groups that may react with a curing agent to form a cured product.

For example when the reactive polyester resin has a carboxyl group at the terminal, curing agent is preferably an epoxy compound having an epoxy such as epoxy resin or acrylic resin containing a glycidyl group. When the reactive polyester resin has a hydroxyl group at the terminal the curing agent may be an isocyanate compound such as aliphatic polyisocyanate and a blocked isocyanate compound or an amino compound.

Hydroxyl-terminated polyesters are the most common polyols, which are crosslinked through isocyanate groups. Generally, polyester polyols can achieve high solid coatings with great solvent resistance and good adhesion to metals. Polyester resins for coating applications are usually prepared with both aromatic and aliphatic dibasic acids. Isophthalic acid is the principal aromatic dibasic acid used in coatings, and adipic acid is the principal aliphatic diacid. The aromatic diacid compound is used to increase the glass transition temperature (Tg), hardness, and chemical resistance. However, the phenyl ring readily absorbs UV light which limit the photo-oxidative stability of the polyester and the polyester from aromatic acid usually has higher viscosity. The advantage of non-aromatic norbornanyl cyclic acid is that it not only has better weather resistance but also enables the preparation the low VOC (volatile organic compounds) resin with lower viscosity.

According to this invention it is possible to design and synthesize functional polymers with different reactive group, crosslinking density, Tg, soften point, molecular weight by select different dienes, dienophiles and carboxyl compounds. It is possible to adjust Tg of polymers by adjusting the weight ratio of bridged rings in molecules.

According to this invention these new norbornanyl rosin acids can be used to prepare novel polyesters for plastic materials. The structurally hindered nature of the bridged ring makes it has better hydrolysis resistant, higher heat resistance, lower water absorption than linear ester structure.

The norbornanyl rosin compositions with carboxylic acid group have similar physical properties as natural rosin, which is a mixture of monocarboxylic diterpene acids with a soften point from about 70° C. to about 85° C. and an acid number from about 150 to 190 mg KOH/g. With adjustable soften point and acidity, light color and amorphous structure with less tendency to crystallize, the acidic norbornanyl rosin provided in present invention may be used as an synthetic rosin for the manufacture of adhesives, paper sizing agents, printing inks, solders and fluxes, various surface coatings, insulating materials for the electronics industry, synthetic rubber, chewing gums, soaps, and detergents.

If a norbornanyl rosin with dicarboxylic acid groups is reacted with long-chain aliphatic monohydric alcohol a low viscosity oligomeric ester is produced, which can be used as a non-aromatic plasticizers, a compatibilizer, a surface-tension modifier and a pigment dispersing agent. It is also possible to produce pour point depressant for diesel oil, lubricating oil, automatic transmission oil, hydraulic oil, home heating oil, and crude oil. The presence of pour point depressant will allow these oils to flow freely at lower temperatures. The pour point depressant can be prepared by esterification of norbornane acid with alcohol containing long alkyl group.

The cyclic rosin polyester of the present invention may also be useful as a viscosity index improver and a thickening agent for mineral lubricating oil and a synthetic lubricating oil to improve the application properties such as oxidation stability, viscosity index, shear stability, and low-temperature viscosity. To be used as an additive for lubricating oil the cyclic polyester should have a weight average molecular weight (Mw) of 20,000 to 400,000 for the good viscosity index improvement, the shear stability and solubility. To prevent corrosion and poor solubility, the polyester should have an acid value less than 5 mg KOH/g and a hydroxyl value less than 20 mg KOH/g.

It is possible to use this norbornanyl rosin carboxylic acid to prepare a polycarbonate diol, which is suitable for polyurethane based adhesives and coating. Polycarbonate diol is prepared from the transesterification reaction of cyclic polyester diol with carbonate such as dimethyl carbonate.

Acrylic esters or methacrylic esters of cyclic rosin polyester diol or polyol can be prepared by the esterification reaction of acrylic acid or methacrylic acid. Acrylic polyester containing a polycyclic hydrocarbon skeleton in the molecule is a curable resin and can be used for weathering-stable coating or adhesives that cure at high rates when exposed to radiation or free radicals.

The norbornanyl rosin resin actually is a hybrid resin of rosin and hydrocarbon resin or petroleum resin. It will be useful as a modified hydrocarbon resin or petroleum resin, which are commonly made by polymerization of unsaturated aliphatic petroleum hydrocarbon feedstocks. Compared with traditional hydrocarbon resins the norbornanyl rosin resin has light color and better weathering-stability. It is easy to achieve desirable balance of the acid number, melt viscosity, softening point, polarity, rigidity, alkyd compatibility, pigment dispersibility etc. by properly adjusting the reaction conditions and the structures of diene, dienophile and carboxylic acid. With the properties similar to hydrocarbon resin or petroleum resin the novel norbornanyl rosin resin can be useful as tackifier or binder for a lot of applications, such as hot-melt adhesive, pressure sensitive adhesives, sealant, traffic paint, or printing ink.

One of the possible applications for this novel norbornanyl rosin acid based polyester is preparation of amorphous polyester resin. The esterification of norbornanyl rosin acid and terephthalate with ethylene glycol or just blending amorphous norbornanyl rosin polyester with crystalline polyethylene terephthalate (PET) may disrupt the crystalline structure and produce an amorphous polyester composition. The amorphous polyesters are widely used for packaging materials or extruded objects due to their higher optical clarity, impact resistance, and ease processing.

The present invention relates to a rosin based polyesterimide containing bulky bridged cyclic hydrocarbon skeleton, which offers high glass transition temperature, low coefficient of linear thermal expansion. Polyimide is a known polymer with outstanding heat stability and mechanical property but it is hard to be processed and not available for application in solution processing because it is insoluble in general organic solvents or monomers. The incorporation of ester section makes the polyesterimide soluble in reactive solvents. The novel rosin polyesterimide with good heat stability, filming ability and solubility produced in this invention is easy to be processed and will be useful in producing insulating coating of magnet wire, toner composition etc.

Usually the aliphatic polyamides are made with linear dicarboxylic acid such as adipic acid for nylon-66. One disadvantage of these linear aliphatic polyamides is that it may undergo dimensional and stiffness change due to moisture absorption. Rosin based aliphatic polyamides contain bulky cyclic norbornane structure and are less susceptible to moisture absorption and may lead to a new type of nylon with better stability of dimension and stiffness.

The synthetic strategy of this invention involving Diels-Alder reaction and acid addition not only provides great application opportunities in rosin modification but also opens a door for green chemistry. For example biobased acrylic acid, fumaric acid, maleic acid, furan, itaconic acid can be used for Diels-Alder adduct for rosin modification. Thus, more green ink, adhesive, plastics or coating can now be made from renewable sources, which reduces consumption of petroleum based starting materials.

EXAMPLE

The following Examples are being supplied to further define various species of the present invention, it being noted that these examples are intended to illustrate and not limit the scope of the present invention. Parts and percentages are by weight unless otherwise indicated.

Viscosity was measured by Brookfield Viscometer. Softening point was measured by LP-16 Softening Point Ring and Ball Apparatus.

Color was measured by Gardner Delta Color Comparator in 50% resin solids in toluene.

The molecular weight is measured by the gel permeation chromatography (GPC).

Gel time test involves determining the gel time, cure time and peak temperature for a formulation catalyzed with 1% benzoyl peroxide maintained at 180° F. (82.2° C.) in a water bath. The gel time is defined as the time required to go from 150° to 190° F. The cure time is defined as the time from 190° F. to the peak temperature (the total time to peak is the sum of the two), and peak temperature (or peak exotherm) is the maximum temperature attained by the sample during cure. These parameters are a representation of the lead time, reactivity and rate of cure for any curable formulation.

The Abbreviations used in the example are as follows.
DCPD: Dicyclopentadiene (95%)
Nadic anhydride: 5-Norbornene-2,3-dicarboxylic anhydride
$NBCO_2H$: 5-Norbornene-2-carboxylic acid
NPG: Neopentyl glycol
PG: Propylene glycol
EG: Ethylene glycol
THQ: Toluhydroquinone
Pine gum rosin available from Diamond G Forest Products, had an acid value of 158 mg KOH/g; Softening point (R and B): 73° C.; Colour (Garder; 50% toluene): 4.

Specific Embodiments

Example 1

Preparation of 5-norbornene-2,3-dicarboxylic Acid ($NBCO_2H$)

To a three-neck, round-bottom flask equipped with a mechanical stirrer, a Dean-Stark trap, a nitrogen inlet, and a water condenser were charged freshly distilled cyclopentadiene (198.3 g, 3.0 moles) was added to a solution of freshly distilled acrylic acid (216.2 g, 3.0 moles). The solution had a temperature between 5° C. and 10° C. The exothermic reaction was controlled by an ice bath. The cyclopentadiene was added to the solution over a period of one hour and after all the cyclopentadiene had been added, the solution was allowed to warm to ambient temperature. After a reaction period of 16 hours, gas chromatographic (GC) analysis indicated a $NBCO_2H$ mixture of isomers with 83% purity and about 2% adduct of cyclopentadiene and acrylic acid dimer.

Example 2

Preparation of $NBCO_2H$-Rosin

Gum rosin (45.3 g), and $NBCO_2H$ (21.7 g) prepared in Example 1 were charged to a flask equipped with a nitrogen inlet, stirrer, condenser and thermocouple. The flask contents were heated slowly until they reached 230° C. in 1 hour and then maintained for 5 hours. The reaction mixture was then poured on to a foil lined tray and allowed to cool before being broken up in to small pieces. The product had an acid value of 147 mg KOH/g; Softening point (R and B): 132° C.; Colour (Gardner; 50% toluene): 8.

Example 3

Preparation of $NBCO_2H$-Rosin

Gum rosin (137.0 g), and $NBCO_2H$ (27.6 g) prepared in Example 1 were charged to a flask equipped with a nitrogen inlet, stirrer, condenser and thermocouple. The flask contents were heated slowly until they reached 160° C. and then this temperature was maintained for one hour. The temperature was then increased to 250° C. in 4 hours and then maintained for 2 hours. The reaction mixture was then poured on to a foil lined tray and allowed to cool before being broken up in to small pieces. The product had an acid value of 156 mg KOH/g; Softening point (R and B): 109° C.; Colour (Gardner; 50% toluene): 11.

Example 4

Preparation of $NBCO_2H$ Oligomer-Rosin $NBCO_2H$ (103.0 g) was heated to 200-225° C. and held for 15 hours under nitrogen to obtain a cyclic oligomeric carboxylic acid with an acid number of 110 mg KOH/g. Then after cool to 150° C. gum rosin (103.0 g) was added. The temperature was then increased to 250° C. in 1 hour and then maintained for 3 hours. The reaction mixture was then poured on to a foil lined tray and allowed to cool before being broken up in to small pieces. The product had an acid value of 118 mg KOH/g; Softening point (R and B): 123° C.; Colour (Gardner; 50% toluene): 6.

Example 5

Preparation of NBCO$_2$H/DCPD Oligomer-Rosin

NBCO$_2$H (54.0 g) and DCPD (26.0 g) was heated to 200° C. in 3 hours and held for 2 hours under nitrogen to obtain a cyclic oligomeric carboxylic acid with an acid number of 280 mg KOH/g. Then after cool to 150° C. gum rosin (134.0 g) was added. The temperature was then increased to 250° C. in 3 hour and then maintained for 2 hours. The product had an acid value of 153 mg KOH/g; Softening point (R and B): 113° C.; Colour (Gardner; 50% toluene): 10.

Example 6

Preparation of NBCO$_2$H/DCPD/AA-Rosin by One-Pot Process

Gum rosin (137.0 g) was heated slowly until they reached 230° C. in 2 hours and then this temperature was maintained for 2 hours. Then the solution of DCPD (53.0 g), acrylic acid (58.0 g) and THQ (0.17 g) was dropped into the rosin within 1 hour at 220-230° C., and then maintained for 7 hours. The product had an acid value of 158 mg KOH/g; Softening point (R and B): 129° C.; Colour (Gardner; 50% toluene): 13.

Example 7

Preparation of NBCO2H/DCPD/AA-Rosin by One-Pot Process

Gum rosin (103.0 g) was heated slowly until they reached 220° C. in 1 hour and then this temperature was maintained for 2 hours. Then the solution of DCPD (40.0 g), acrylic acid (22.0 g) and THQ (0.08 g) was dropped into the rosin within 5 hour at 220-230° C., then temperature was increased to 240° C. and maintained for 9 hours. The product had an acid value of 150 mg KOH/g; Softening point (R and B): 122° C.; Colour (Gardner; 50% toluene): 14.

Example 8

Preparation of NBCO$_2$H/DCPD/AA-Rosin by One-Pot Process

Gum rosin (137.0 g) was heated slowly until they reached 220° C. in 1 hour and then this temperature was maintained for 2 hours. Then the solution of DCPD (40.0 g), acrylic acid (43.0 g) and THQ (0.10 g) was dropped into the rosin within 4 hours at 240-250° C., then temperature was maintained for 6 hours. The product had an acid value of 179 mg KOH/g; Softening point (R and B): 121° C.; Colour (Gardner; 50% toluene): 5.

Example 9

Preparation of NBCO$_2$H/DCPD/AA-Rosin by One-Pot Process

Gum rosin (137.0 g) was heated slowly until they reached 240° C. in 1 hour and then this temperature was maintained for 1 hour. Then the solution of DCPD (13.2 g), acrylic acid (14.4 g) and THQ (0.10 g) was dropped into the rosin within 1 hour at 240-250° C., then temperature was maintained for 4 hours. The product had an acid value of 155 mg KOH/g; Softening point (R and B): 105° C.; Colour (Gardner; 50% toluene): 9.

Example 10

Preparation of NBCO$_2$H/DCPD/AA-Rosin by One-Pot Process

Gum rosin (137.0 g) was heated slowly until they reached 240° C. in 1 hour and then this temperature was maintained for 1 hour. Then the solution of DCPD (79.2 g), acrylic acid (57.6 g) and THQ (0.17 g) was dropped into the rosin within 3 hour at 235-240° C. then temperature was maintained for 4 hours. The product had an acid value of 148 mg KOH/g; Softening point (R and B): 122° C.; Colour (Gardner; 50% toluene): 8. The same product (100.0 g) was heated to 210° C. in vacuum (about 25") to remove volatile materials such as the unreacted materials and low boiling substances (8.0 g) to obtain a final product having an acid value of 136 mg KOH/g; Softening point (R and B): 139° C.; Colour (Gardner; 50% toluene): 10.

Example 11

Preparation of Nadic Anhydride-Rosin

Gum rosin (68.0 g) was heated slowly until they reached 200° C. in 1 hour and then this temperature was maintained for 1 hour. Then temperature was lowered to 120° C. and nadic anhydride (32.6 g) was added into the rosin, then temperature was increased to 230° C. and maintained for 5 hours. The product had an acid value of 165 mg KOH/g; Softening point (R and B): 140° C.; Colour (Gardner; 50% toluene): 12, molecular weight of Mw/Mn=746/367

Example 12

Preparation of DCPD/MAn-Rosin by One-Pot Process

Gum rosin (45.3 g) was heated slowly until they reached 220° C. in 1 hour and then this temperature was maintained for 1 hour and cool to 130° C. then DCPD (8.8 g) and maleic anhydride (13.0 g) was added into the rosin. The temperature was increased to 220° C. and maintained for 5 hours. The product had an acid value of 174 mg KOH/g; Softening point (R and B): 125° C.

Example 13

Preparation of NBCO$_2$H/DCPD/AA-Rosin Based Polyester by One-Pot Process

Gum rosin (60.0 g) was heated slowly until they reached 220° C. in 1 hour and then this temperature was maintained for 1 hour. Then the solution of DCPD (26.0 g), acrylic acid (14.2 g) and THQ (0.07 g) was dropped into the rosin within 4 hour at 200-220° C. then temperature was maintained for 4 hours to an acid value of 148 mg KOH/g; NPG (20.0 g) was added and heat to 200-220° C. to an acid value 38 mg KOH/g; the polyester had an Softening point (R and B): 111° C.

Example 14

Preparation of NBCO$_2$H/DCPD/AA-Rosin Based Polyester by One-Pot Process

Gum rosin (72.0 g) was heated slowly until they reached 200° C. in 1 hour and then this temperature was maintained for 2 hour. Then the solution of DCPD (14.0 g), acrylic acid (15.0 g) and THQ (0.07 g) was dropped into the rosin within 4 hour at 200-220° C., then temperature was maintained for 2 hours to an acid value of 197 mg KOH/g; PG (93.0 g) was added and heat to 190-200° C. and hold for 10 hours. Maleic anhydride (80.0 g) was added and heat to 210-215° C. and hold to an acid value 31 mg KOH/g; The resulting polyester was dissolved in styrene with 0.07 g of THQ to obtain a resin with 40% styrene, it has a viscosity of 860 cps and a gel time 24 min, cure time 26 min and peak exotherm 208° C.

Example 15

Preparation of Nadic Imide-Rosin Based Polyesterimide by One-Pot Process

Nadic anhydride (82.1 g) was dissolved in 105 ml of toluene. To the mixture was slowly added ethanolamine (30.6 g) at 30-70° C. and then stirred for 3 hours at 100-130° C. to remove water and part of toluene. Rosin (171.0 g) was added and the mixture was heated to 240° C. in 4 hours. The reaction was kept at 240-250° C. until an acid number of 54 mg KOH/g was obtained. The obtained polyesterimide had an Softening point (R and B): 114° C.

Example 16

Preparation of TMPTA/DCPD-Rosin

Gum rosin (103.0 g) was heated slowly until they reached 250° C. in 1 hour and then this temperature was maintained for 1 hour. Then the solution of DCPD (20.0 g), trimethylolpropane triacrylate (30.0 g) and THQ (0.07 g) was dropped into the rosin within 20 minutes at 250° C., then temperature was maintained for 2 hours to an acid value of 64 mg KOH/g; product had a Softening point (R and B): 117° C.; Colour (Gardner; 50% toluene): 5.

Example 17

Preparation of Furfuryl Alcohol/AA-Rosin

Gum rosin (103.0 g) was heated slowly until they reached 250° C. in 1 hour and then this temperature was maintained for 1 hour. Then the solution of furfuryl alcohol (29.4 g), acrylic acid (22.0 g) and THQ (0.07 g) was dropped into the rosin within 2 hours at 230-240° C., then temperature was maintained for 2 hours to an acid value of 176 mg KOH/g; product had an Softening point (R and B): 104° C.

Example 18

Preparation of MAc/DCPD-Rosin

Maleic anhydride (39.2 g), water (8.0 g) and DCPD (53.0 g) were heated to 120° C. in 2 hours under nitrogen and held at 110-125° C. for 3 hours to obtain a DCPD maleic half-ester with a an acid value of 212 mg KOH/g.

Gum rosin (137.0 g) was heated slowly until they reached 250° C. in 1 hour and then this temperature was maintained for 1 hour and cool to 120° C. then the obtained DCPD maleic half-ester was added into the rosin, the temperature was increased to 230-240° C. in 2 hours and maintained for 2 hours to an acid value of 141 mg KOH/g; product had an Softening point (R and B): 108° C.; Colour (Gardner; 50% toluene): 10.

Example 19

Preparation of NBCO$_2$H/DCPD/Mac-Rosin

NBCO$_2$H (52.0 g) and DCPD (25.0 g) was heated to 200° C. in 3 hours and held for 2 hours under nitrogen. Then after cool to 120° C. maleic acid (43.0 g) was added. The temperature was maintained in 115-125° C. in 4 hour and then gum rosin (127.0 g) was added, the temperature was increased to 225° C. in 2 hours and maintained 2 hours. The product had an acid value of 212 mg KOH/g; Softening point (R and B): 123° C.; Colour (Gardner; 50% toluene): 11.

What is claimed is:

1. A norbornanyl rosin resin composition comprising the reaction products of a predominant amount of rosin derivative and lesser amount of norbornenyl compound, where the norbornenyl compound is selected from the group consisting of

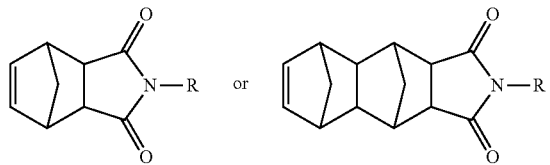

wherein R is selected from the group consisting of hydrogen; halogen; hydroxyl; acid (—C(O)OH); ester (—C(O)OR$_a$); formate (—OC(O)H); acid halide (—C(O)Z); aldehyde (—C(O)H); ketone (—C(O)R$_a$); nitro (—NO$_2$); carboxamide (—C(O)NR$_a$R$_b$); amine (—NR$_a$R$_b$); silicone (—SiR$_a$R$_b$R$_c$); cyano (—CN); isocyanate (—NCO); alkoxy (—OR$_a$); phosphonate (—P(O)R$_a$R$_b$); unsubstituted or substituted C$_1$-C$_{100}$ alkyl group, unsubstituted or substituted C$_2$-C$_{100}$ alkenyl group, unsubstituted or substituted C$_2$-C$_{100}$ alkynyl group, unsubstituted or substituted C$_3$-C$_{100}$ cycloalkyl group, unsubstituted or substituted C$_6$-C$_{100}$ aryl group, when it is substituted with one or more substituent group the substituent group may be a carboxyl, hydroxyl, thiol, halogen, ester, amine, amide, imide, isocyanate, alkyl, alkenyl, alkynyl, haloalkyl, haloalkenyl, haloalkynyl, aryl, haloaryl, aralkyl, haloaralkyl, alkoxy, haloalkoxy, halocarbonyloxy, aryloxy, haloaryloxy, silyl, siloxy, glycidoxy, heterocyclo, carbonate, carboxylate, or quaternary ammonium; R$_a$, R$_b$ and R$_c$ are independently hydrocarbyl, substituted hydrocarbyl; Z is a halogen atom.

2. A norbornanyl rosin resin composition comprising the reaction products of a predominant amount of rosin derivative and lesser amount of norbornenyl compound, where the norbornenyl compound is selected from the group consisting of

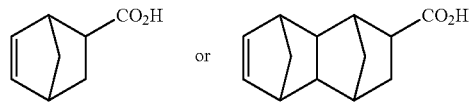 [SMILES: O=C(O)C1CC2C=CC1C2 ; O=C(O)C1CC2CC1C1C3C=CC(C3)C21]

3. A norbornanyl rosin resin composition comprising the reaction products of a predominant amount of rosin derivative and lesser amount of norbornenyl compound, where the norbornenyl compound is selected from the group consisting of

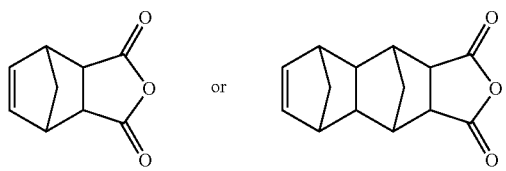 [SMILES: O=C1OC(=O)C2C3C=CC(C3)C12 ; O=C1OC(=O)C2C3CC(C12)C1C2C=CC(C2)C31]

* * * * *